(12) United States Patent
Perron et al.

(10) Patent No.: US 6,692,730 B2
(45) Date of Patent: Feb. 17, 2004

(54) WASHING COMPOSITION COMPRISING PARTICLES OF ALUMINUM OXIDE, AT LEAST ONE CONDITIONING AGENT AND AT LEAST ONE DETERGENT SURFACTANT

(75) Inventors: Béatrice Perron, Jouy en Josas (FR); Serge Restle, Saint Prix (FR); Franck Giroud, Clichy (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/955,025

(22) Filed: Sep. 19, 2001

(65) Prior Publication Data

US 2002/0054862 A1 May 9, 2002

(30) Foreign Application Priority Data

Sep. 20, 2000 (FR) .............................. 00 11993

(51) Int. Cl.$^7$ .............................. A61K 6/00; A61K 7/00; A61K 7/06; A61K 7/075; A61K 7/08
(52) U.S. Cl. .................. 424/70.12; 424/70.1; 424/401; 424/70.19; 424/70.21; 424/70.22
(58) Field of Search .............................. 424/401, 70.21, 424/70.22, 70.1, 70.19, 70.12

(56) References Cited

U.S. PATENT DOCUMENTS 3,819,827 A * 6/1974 Berger .......................... 424/70
5,393,519 A * 2/1995 Dowell et al. ........... 424/70.11

* cited by examiner

*Primary Examiner*—Thurman K. Page
*Assistant Examiner*—S. Howard
(74) *Attorney, Agent, or Firm*—Steptoe & Johnson LLP; D. Douglas Price

(57) ABSTRACT

The present invention relates to a composition for washing keratinous materials, in particular hair, which comprises, in a cosmetically acceptable medium, particles essentially consisting of aluminium oxide and having a mean primary size in numerical terms of less than 200 nm, at least one conditioning agent chosen from cationic surfactants, cationic polymers, silicones, vegetable oils, ceramides, anionic polymers, amphoteric polymers and mixtures thereof, and at least one detergent surfactant, these compositions not simultaneously containing an anionic surfactant and an amphoteric or nonionic surfactant. The invention also relates to a method for the cosmetic treatment of keratinous fibres, and a use of the composition according to the invention as a shampoo.

24 Claims, No Drawings

WASHING COMPOSITION COMPRISING PARTICLES OF ALUMINUM OXIDE, AT LEAST ONE CONDITIONING AGENT AND AT LEAST ONE DETERGENT SURFACTANT

The present invention relates to a composition for washing keratinous materials, in particular hair, comprising particles essentially consisting of aluminium oxide, at least conditioning agent and at least one detergent surfactant, to a method for the cosmetic treatment of keratinous fibres and to a use of the composition as a shampoo.

U.S. Pat. No. 3,819,827 by WELLA describes, in particular, products for hair setting comprising from 0.2 to 6% by weight of particles of aluminium oxide having a particle size of about 30 mµ, and from 1 to 4% by weight of polymers such as gum tragacanth, agar, pectin, vinyl polymers and basic polymers.

The applicant has found, surprisingly, that the use of particles essentially consisting of aluminium oxide and having a mean primary size in numerical terms of less than 200 nm, with a particular conditioning agent and at least one detergent surfactant in washing compositions, made it possible to obtain good form retention and a certain volume of the hair, that is to say a hair styling effect. It is observed, moreover, that the keratinous fibres have become firm and strong.

The subject of the present invention is therefore a composition for washing keratinous materials, in particular hair, comprising, in a cosmetically acceptable aqueous medium, particles essentially consisting of aluminium oxide and having a mean primary size in numerical terms of less than 200 nm, at least one particular conditioning agent and at least one detergent surfactant.

Another subject of the invention consists in a method for the cosmetic treatment of keratinous fibres using the composition according to the invention.

The subject of the invention is also a use of the composition according to the invention as a shampoo.

Other subjects, characteristics, aspects and advantages of the invention will appear more clearly on reading the description and the various examples which follow.

According to the invention, the composition for washing keratinous materials, in particular hair, comprises, in a cosmetically acceptable aqueous medium, particles essentially consisting of aluminium oxide and having a mean primary size in numerical terms of less than 200 nm, at least one conditioning agent chosen from cationic surfactants, cationic polymers, silicones, vegetable oils, ceramides, anionic polymers, amphoteric polymers and mixtures thereof, and at least one detergent surfactant, these compositions not simultaneously containing an anionic surfactant and an amphoteric or nonionic surfactant.

The expression "cosmetically acceptable aqueous medium" is understood to mean a medium compatible with keratinous materials such as the skin and the hair.

The expression "particles essentially consisting of aluminium oxide" is understood to mean particles consisting of more than 90% by weight of aluminium oxide.

For the purposes of the present invention, the expression "primary size of a particle" is understood to mean the maximum size which it is possible to measure between two diametrically opposite points of an individual particle. The size may be determined by transmission electron microscopy or from the measurement of the specific surface area by the BET method.

The mean primary size in numerical terms of the particles is preferably between 5 and 50 nm, and more preferably still between 5 and 25 nm.

The particles of aluminium oxide according to the invention essentially consist of any optionally hydrated aluminium oxide such as, for example, boehmite.

The particles may have any shape different from plates, for example a shape of a sphere, flakes, needles or plates, and preferably they are substantially spherical.

The particles of aluminium oxide may be used in the composition according to the invention in a quantity ranging from 0.01 to 20% by weight, preferably from 0.1 to 5% by weight, relative to the total weight of the washing composition of the invention.

The detergent surfactants which can be used in the present invention are in particular chosen from anionic, amphoteric and nonionic surfactants, provided that an anionic surfactant and an amphoteric or nonionic surfactant are not simultaneously used.

As anionic surfactants which can be used in the present invention, there may be mentioned especially salts, in particular alkali metal salts such as sodium salts, ammonium salts, amine salts, amino alcohol salts or salts of alkaline earth metals, for example magnesium, of the following types: alkyl sulphates, alkyl ether sulphates, alkyl amidoether sulphates, alkyl aryl polyether sulphates, monoglyceride sulphates; alkyl sulphonates, alkyl amide sulphonates, alkyl aryl sulphonates, α-olefin sulphonates, paraffin sulphonates; alkyl sulphosuccinates, alkyl ether sulphosuccinates, alkyl amide sulphosuccinates; alkyl sulphoacetates; acyl sarcosinates; and acyl glutamates, the alkyl and acyl groups of all these compounds comprising from 6 to 24 carbon atoms and the aryl group preferably denoting a phenyl or benzyl group. It is also possible to use the esters of a $C_6$–$C_{24}$ alkyl and polyglycoside carboxylic acids such as alkyl glucoside citrates, alkyl polyglycoside tartrates and alkyl polyglycoside sulphosuccinates; alkyl sulphosuccinamates, acyl isethionates and N-acyltaurates, the alkyl or acyl group of all these compounds comprising from 12 to 20 carbon atoms. Among the anionic surfactants which can also be used, there may also be mentioned acyl lactylates in which the acyl group comprises from 8 to 20 carbon atoms.

In addition, there may also be mentioned alkyl D-galactoside uronic acids and their salts as well as polyoxyalkylenated ($C_6$–$C_{24}$)alkyl ether carboxylic acids, polyoxyalkylenated ($C_6$–$C_{24}$) alkyl ($C_6$–$C_{24}$) aryl ether carboxylic acids, polyoxyalkylenated ($C_6$–$C_{24}$)alkyl amidoether carboxylic acids and their salts, in particular those comprising from 2 to 50 ethylene oxide groups, and mixtures thereof.

The anionic surfactants as described above may be used alone or as a mixture. Alkyl sulphates, alkyl ether sulphates and alkyl ether carboxylates and mixtures thereof, in particular in the form of their alkali or alkaline earth metal, ammonium, amine or amino alcohol salts, are preferably used.

The amphoteric surfactants which are suitable in the present invention may be in particular secondary or tertiary aliphatic amine derivatives in which the aliphatic group is a linear or branched chain comprising from 8 to 22 carbon atoms and containing at least one water-solubilizing anionic group such as, for example, a carboxylate, sulphonate, sulphate, phosphate or phosphonate group; there may also be mentioned ($C_8$–$C_{20}$)alkylbetaines, sulphobetaines, ($C_8$–$C_{20}$) alkylamido ($C_6$–$C_8$) alkylbetaines or ($C_8$–$C_{20}$) alkylamido($C_6$–$C_8$)alkylsulphobetaines, and mixtures thereof.

Among the amine derivatives, there may be mentioned the products marketed under the name MIRANOL®, as described in U.S. Pat. Nos. 2,528,378 and 2,781,354 and classified in the CTFA dictionary, 3rd edition, 1982, under the names Amphocarboxyglycinate and Amphocarboxypropionate having the respective structures (1) and (2):

$$R_a-CONHCH_2CH_2-N(R_b)(R_c)(CH_2COO^-) \quad (1)$$

in which:

$R_a$ represents an alkyl group derived from an acid $R_a$—COOH present in hydrolysed copra oil, a heptyl, nonyl or undecyl group, $R_b$ represents a beta-hydroxyethyl group, and $R_c$ represents a carboxymethyl group; and $$R_{a'}-CONHCH_2CH_2-N(B)(C) \quad (2)$$

in which:

B represents —CH$_2$CH$_2$OX',

C represents —(CH$_2$)$_z$—Y', with z=1 or 2,

X' represents a group —CH$_2$CH$_2$—COOH or a hydrogen atom,

Y' represents —COOH or a group —CH$_2$—CHOH—SO$_3$H, $R_{a'}$ represents an alkyl group of an acid $R_{a'}$—COOH present in copra oil or in hydrolysed linseed oil, an alkyl group, in particular a $C_{17}$ and its iso form, an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylomphodiacetate, disodium cocoamphodipropionate, disodium lauroamphodipropionate, disodium caprylamphodipropionate, disodium caprylomphodipropionate, lauroamphodipropionic acid, cocoamphodipropionic acid.

By way of example, there may be mentioned the cocoamphodiacetate marketed under the trade name MIRANOL® C2M concentrate by the company RHODIA.

The nonionic surfactants suitable in the invention are compounds which are well known per se (see in particular in this regard "Handbook of Surfactants" by M. R. PORTER, published by Blackie & Son (Glasgow and London), 1991, pp. 116–178). Thus, they may be chosen in particular from alcohols, alpha-diols, ($C_1$–$C_{20}$)alkylphenols or polyethoxylated, polypropoxylated or polyglycerolated fatty acids, having a fatty chain comprising, for example, from 8 to 18 carbon atoms, it being possible for the number of ethylene oxide or propylene oxide groups to range in particular from 2 to 50 and it being possible for the number of glycerol groups to range in particular from 2 to 30. There may also be mentioned copolymers of ethylene and propylene oxides, condensates of ethylene and propylene oxides with fatty alcohols; polyethoxylated fatty amides preferably having from 2 to 30 mol of ethylene oxide, polyglycerolated fatty amides comprising on average 1 to 5 glycerol groups and in particular 1.5 to 4; the polyethoxylated fatty amines preferably having 2 to 30 mol of ethylene oxide; the ethoxylated fatty acid esters of sorbitan having from 2 to 30 mol of ethylene oxide; the fatty acid esters of sucrose, the fatty acid esters of polyethylene glycol, the ($C_6$–$C_{24}$)alkyl polyglycosides, the N-($C_6$–$C_{24}$)alkylglucamine derivatives, the amine oxides such as the ($C_{10}$–$C_{14}$)alkylamine oxides or the N-($C_{10}$–$C_{14}$)acylaminopropylmorpholine oxides, and mixtures thereof.

Among the nonionic surfactants cited above, ($C_6$–$C_{24}$) alkyl polyglycosides are preferably used.

The anionic surfactants, the amphoteric or nonionic surfactants may be used in the composition of the present invention in a total quantity of between 1 and 50% by weight, preferably of between 5 and 35% by weight and better still of between 8 and 25% by weight, relative to the total weight of the composition.

The composition according to the invention also comprises at least one conditioning agent chosen from cationic surfactants, cationic polymers, silicones, vegetable oils, ceramides, anionic polymers, amphoteric polymers and mixtures thereof.

The composition according to the invention may comprise one or more cationic surfactants well known per se, such as the salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides with a cationic character.

The composition according to the invention may comprise one or more cationic polymers.

The expression cationic polymer is understood to mean any polymer containing cationic groups and/or groups which can be ionized into cationic groups.

The cationic polymers which can be used in accordance with the present invention may be chosen from all those already known per se to improve the cosmetic properties of hair treated with detergent compositions, namely in particular those described in patent application EP-A-0 337 354 and in French patent applications FR-A-2 270 846, 2 383 660, 2 598 611, 2 470 596 and 2 519 863.

The preferred cationic polymers are chosen from those which contain units comprising primary, secondary, tertiary and/or quaternary amine groups which may either form part of the principal polymer chain, or which may be carried by a side substituent directly linked thereto.

The cationic polymers used generally have a number-average molecular mass of between 500 and $5 \times 10^6$ approximately, and preferably of between $10^3$ and $3 \times 10^6$ approximately.

Among the cationic polymers, there may be mentioned more particularly the polymers of the polyamine, polyaminoamide and poly(quaternary ammonium) type. They are known products.

The polymers of the polyamine, polyaminoamide and poly(quaternary ammonium) type which can be used in the composition of the present invention, are those described in French Patents No. 2 505 348 or 2 542 997. Among these polymers, there may be mentioned:

(1) the homopolymers or copolymers derived from acrylic or methacrylic esters or amides and comprising at least one of the units of the following formulae:

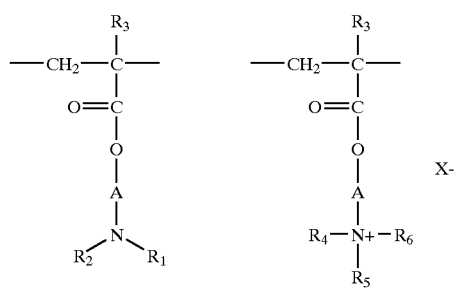

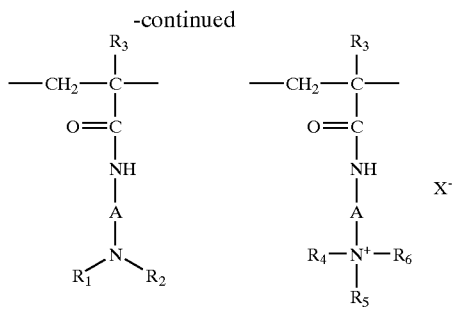

in which:

R$_3$, which are identical or different, denote a hydrogen atom or a CH$_3$ group;

A, which are identical or different, represent a linear or branched alkyl group comprising from 1 to 6 carbon atoms, preferably 2 or 3 carbon atoms or a hydroxyalkyl group comprising from 1 to 4 carbon atoms;

R$_4$, R$_5$, R$_6$, which are identical or different, represent an alkyl group having from 1 to 18 carbon atoms or a benzyl group and preferably an alkyl group having from 1 to 6 carbon atoms;

R$_1$ and R$_2$, which are identical or different, represent hydrogen or an alkyl group having from 1 to 6 carbon atoms and preferably a methyl or ethyl group;

X denotes an anion derived from an inorganic or organic acid such as a methosulphate anion or a halide such as chloride or bromide.

The copolymers of the family (1) may contain, in addition, one or more units derived from comonomers which may be chosen from the family of acrylamides, methacrylamides, diacetone acrylamides, acrylamides and methacrylamides substituted on the nitrogen with lower (C$_1$–C$_4$)alkyls, groups derived from acrylic or methacrylic acids or esters thereof, vinyllactams such as vinylpyrrolidone or vinylcaprolactam, vinyl esters.

Thus, among these copolymers of the family (1), there may be mentioned:

- the copolymers of acrylamide and dimethylaminoethyl methacrylate quaternized with dimethyl sulphate or with a dimethyl halide such as that sold under the name HERCOFLOC® by the company HERCULES,
- the copolymers of acrylamide and methacryloyloxyethyltrimethylammonium chloride described, for example, in Patent Application EP-A-080976 and sold under the name BINAQUAT® P 100 by the company CIBA GEIGY,
- the copolymer of acrylamide and methacryloyloxyethyltrimethylammonium methosulphate sold under the name RETEN by the company HERCULES,
- the vinylpyrrolidone/dialkylaminoalkyl acrylate or methacrylate copolymers, quaternized or otherwise, such as the products sold under the name "GAFQUAT®" by the company ISP such as for example "GAFQUAT® 734" or "GAFQUAT® 755" or alternatively the products called "COPOLYMER 845, 958 and 937". These polymers are described in detail in French Patents 2,077,143 and 2,393,573,
- the dimethylaminoethyl methacrylate/vinylcaprolactam/vinylpyrrolidone terpolymers such as the product sold under the name GAFFIX® VC 713 by the company ISP,
- the vinylpyrrolidone/methacrylamidopropyldimethylamine copolymers marketed in particular under the name STYLEZE® CC 10 by ISP, and
- the quaternized vinylpyrrolidone/dimethylaminopropyl methacrylamide copolymers such as the product sold under the name "GAFQUAT® HS 100" by the company ISP.

(2) The cellulose ether derivatives comprising quaternary ammonium groups, described in French Patent 1,492,597, and in particular the polymers marketed under the names "JR" (JR 400, JR 125, JR 30M) or "LR" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described especially in U.S. Pat. No. 4,131,576, such as hydroxyalkyl celluloses like hydroxymethyl, hydroxyethyl or hydroxypropyl celluloses grafted especially with a methacryloylethyltrimethylammonium, methacrylamidopropyltrimethylammonium or dimethyldiallylammonium salt.

The commercialized products corresponding to this definition are more particularly the products sold under the name "Celquat® L 200" and "Celquat® H 100" by the company National Starch.

(4) The cationic polysaccharides described more particularly in U.S. Pat. Nos. 3,589,578 and 4,031,307 such as guar gums containing cationic trialkylammonium groups. Guar gums modified with a 2,3-epoxypropyltrimethylammonium salt (e.g. chloride) are for example used.

Such products are marketed in particular under the trade names JAGUAR® C13 S, JAGUAR® C 15, JAGUAR® C 17 or JAGUAR® C162 by the company MEYHALL.

(5) Polymers consisting of piperazinyl units and of alkylene or hydroxyalkylene divalent groups with straight or branched chains, optionally interrupted by oxygen, sulphur or nitrogen atoms or by aromatic or heterocyclic rings, as well as the oxidation and/or quaternization products of these polymers. Such polymers are described especially in French patents 2,162,025 and 2,280,361.

(6) Water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or else with an oligomer resulting from the reaction of a difunctional compound which is reactive towards a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described especially in French Patents 2,252,840 and 2,368,508.

(7) Polyaminoamide derivatives resulting from the condensation of polyalkylenepolyamines with polycarboxylic acids, followed by an alkylation with difunctional agents. There may be mentioned, for example, the adipic acid/dialkylaminohydroxyalkyldialkylenetriaminepolymers in which the alkyl group contains from 1 to 4 carbon atoms and preferably denotes a methyl, ethyl or propyl group and the alkylene group contains from 1 to 4 carbon atoms, and preferably denotes the ethylene group. Such polymers are described especially in French Patent 1,583,363.

Among these derivatives there may be mentioned more particularly the adipic acid/dimethylaminohydroxypropyl/ diethylenetriamine polymers sold under the name "Cartaretine® F, F4 or F8" by the compnay Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described especially in U.S. Pat. Nos. 3,227,615 and 2,961,347.

Polymers of this type are marketed in particular under the name "Hercosett® 57" by the company Hercules Inc. or else under the name of "PD 170" or "Delsette® 101" by the company Hercules in the case of the copolymer of adipic acid/epoxypropyl-diethylene-triamine.

(9) Cyclopolymers of alkyldiallylamine or of dialkyldiallylammonium, such as the homopolymers or copolymers comprising, as main constituent of the chain, units corresponding to the formulae (Va) or (Vb):

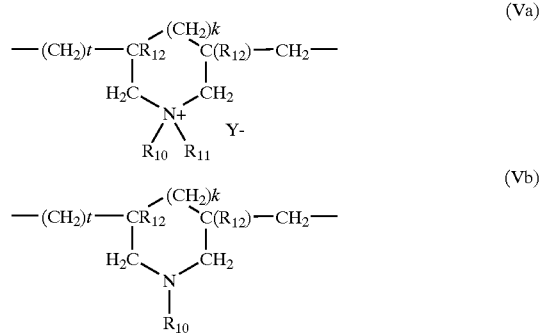

in which formulae k and t are equal to 0 or 1, the sum k+t being equal to 1; $R_{12}$ denotes a hydrogen atom or a methyl group; $R_{10}$ and $R_{11}$, independently of each other, denote an alkyl group containing from 1 to 22 carbon atoms, a hydroxyalkyl group in which the alkyl group preferably has 1 to 5 carbon atoms, or a lower ($C_1$–$C_4$)amidoalkyl group or $R_{10}$ and $R_{11}$ may denote, jointly with the nitrogen atom to which they are attached, heterocyclic groups such as piperidinyl or morpholinyl; $Y^-$ is an anion such as bromide, chloride, acetate, borate, citrate, tartrate, bisulphate, bisulphite, sulphate or phosphate. These polymers are described especially in French Patent 2,080,759 and in its certificate of addition 2,190,406.

$R_{10}$ and $R_{11}$, independently of each other, preferably denote an alkyl group having from 1 to 4 carbon atoms.

Among the polymers defined above there may be mentioned more particularly the dimethyldiallylammonium chloride homopolymer sold under the name "MERQUAT® 100" by the company CALGON (and its homologues of low weight-average molecular masses) and the copolymers of diallyl-dimethylammonium chloride and acrylamide marketed under the name "MERQUAT® 550".

(10) The quaternary diammonium polymers containing repeat

units corresponding to the formula (VI):
in which:

$R_{13}$, $R_{14}$, $R_{15}$ and $R_{16}$, which are identical or different, represent aliphatic, alicyclic or arylaliphatic groups containing from 1 to 20 carbon atoms or lower hydroxyalkyl aliphatic groups, or else $R_{13}$, $R_{14}$, $R_{15}$ and $R_{16}$, together or separately, form, with the nitrogen atoms to which they are attached, heterocyclic rings optionally containing a second heteroatom other than nitrogen, or else $R_{13}$, $R_{14}$, $R_{15}$ and $R_{16}$ denote a linear or branched $C_1$–$C_6$ alkyl group substituted by a nitrile, ester, acyl, amide or —CO—O—$R_{17}$—D or —CO—NH—$R_{17}$—D group where $R_{17}$ is an alkylene group and D a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or several aromatic rings, or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$, with the two nitrogen atoms to which they are attached, may form a piperazine ring; in addition if $A_1$ denotes a saturated or unsaturated, linear or branched alkylene or hydroxyalkylene group, $B_1$ may also denote a group:

—(CH$_2$)$_n$—CO—D—OC—(CH$_2$)$_n$— in which D denotes:

a) a glycol residue of formula: —O—Z—O—, where Z denotes a linear or branched hydrocarbon group or a group corresponding to one of the following formulae:

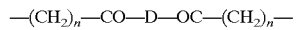

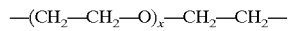

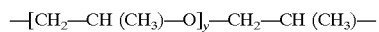

where x and y denote an integer from 1 to 4, representing a defined and unique degree of polymerization or any number from 1 to 4 representing a mean degree of polymerization;

b) a disecondary diamine residue such as a piperazine derivative;

c) a diprimary diamine residue of formula: —NH—Y—NH—, where Y denotes a linear or branched hydrocarbon group or else the divalent group —CH$_2$—CH$_2$—S—S—CH$_2$—CH$_2$—;

d) a ureylene group of formula —NH—CO—NH—.

$X^-$ is preferably an anion such as chloride or bromide.

These polymers have a number-average molecular mass which is generally between 1000 and 100,000.

Polymers of this type are described especially in French Patents 2,320,330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use more particularly the polymers which consist of repeat units corresponding to the formula:

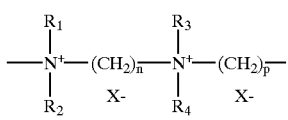

(VII)

in which $R_1$, $R_2$, $R_3$ and $R_4$, which are identical or different, denote an alkyl or hydroxyalkyl group having from 1 to 4 carbon atoms approximately, n and p are integers varying from 2 to 20 approximately and $X^-$ is an anion derived from an inorganic or organic acid.

An especially preferred compound of formula (VII) is that for which $R_1$, $R_2$, $R_3$ and $R_4$ represent a methyl group and n=3, p=6 and X=Cl, called hexadimethrine chloride (CTFA).

(11) Poly(quaternary ammonium) polymers consisting of units

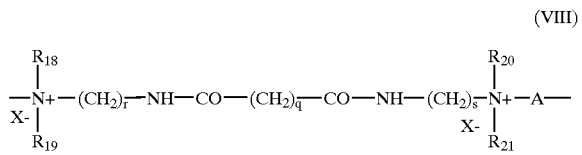

(VIII)

of formula (VIII):
in which:
$R_{18}$, $R_{19}$, $R_{20}$ and $R_{21}$, which are identical or different, denote a hydrogen atom or a methyl, ethyl, propyl, __-hydroxyethyl, __-hydroxypropyl or $-CH_2CH_2(OCH_2CH_2)_pOH$ group, where p is equal to 0 or to an integer between 1 and 6, provided that $R_{18}$, $R_{19}$, $R_{20}$ and $R_{21}$ do not simultaneously denote a hydrogen atom, r and s, which are identical or different, are integers between 1 and 6, q is equal to 0 or to an integer between 1 and 34, $X^-$ denotes an anion such as a halide, A denotes a radical of a dihalide or preferably represents $-CH_2-CH_2-O-CH_2-CH_2-$.

Such compounds are described especially in Patent Application EP-A-122 324.

Among these there may be mentioned, for example, the products "Mirapol® A 15", "Mirapol® AD1", "Mirapol® AZ1" and "Mirapol® 175", sold by the company Miranol.

(12) Quaternary vinylpyrrolidone and vinylimidazole polymers such as, for example, the products marketed under the names Luviquat® FC 905, FC 550 and FC 370 by the company B.A.S.F.

(13) Polyamines like the Polyquart H® sold by Henkel, referred to under the name of "Polyethylene glycol (15) Tallow Polyamine" in the CTFA dictionary.

(14) The crosslinked polymers of methacryloyloxy($C_1$–$C_4$ alkyl)tri($C_1$–$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of the said copolymer in mineral oil. This dispersion is marketed under the name of "SALCARE® SC 92"by the company ALLIED COLLOIDS. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be employed within the scope of the invention are cationic proteins or hydrolysates of cationic proteins, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers capable of being used within the scope of the present invention, it is preferable to use cellulose ether derivatives comprising quaternary ammonium groups such as the products sold under the name "JR 400" by the company UNION CARBIDE CORPORATION, cationic cyclopolymers, in particular the homopolymers or copolymers of dimethyldiallylammonium chloride, sold under the names "MERQUAT® 100", "MERQUAT® 550" and "MERQUAT® S" by the company CALGON, cationic polysaccharides such as guar gums modified by a salt of 2,3-epoxypropyltrimethylammonium, quaternary polymers of vinylpyrrolidone and vinylimidazole, polyquaternary ammonium polycondensates preferably comprising the repeat units of formulae (VI) and (VIII) as indicated above, and mixtures thereof.

Preferably, the composition according to the invention may contain one or more cationic polymers as described above, in a quantity ranging from 0.0001 to 10% by weight, relative to the total weight of the composition. The cationic polymer may then be used in a weight ratio with alumina of between 100 and 0.0005, preferably between 20 and 0.01.

As silicones which can be used in the composition of the present invention, there may be mentioned in particular organomodified or nonorganomodified, branched or unbranched, cyclic or acyclic, volatile or nonvolatile silicones as described below.

The silicones which can be used in accordance with the invention may be soluble or insoluble in the composition and in particular may be polyorganosiloxanes insoluble in the composition of the invention; they may be provided in the form of oils, waxes, resins or gums.

The organopolysiloxanes are defined in greater detail in the book by Walter NOLL "Chemistry and Technology of Silicones" (1968) Academie Press. They may be volatile or nonvolatile.

When they are volatile, the silicones are more particularly chosen from those possessing a boiling point of between 60° C. and 260° C., and more particularly still from:

(i) cyclic silicones comprising from 3 to 7 silicon atoms, and preferably 4 to 5. They are, for example, the octamethylcyclotetrasiloxane marketed in particular under the name "VOLATILE SILICONE 7207" by UNION CARBIDE or "SILBIONE 70045 V 2" by RHODIA, the decamethylcyclopentasiloxane marketed under the name "VOLATILE SILICONE 7158" by UNION CARBIDE, "SILBIONE 70045 V 5" by RHODIA, and mixtures thereof.

There may also be mentioned cyclocopolymers of the dimethylsiloxane/methylalkylsiloxane type, such as the "SILICONE VOLATILE FZ 3109" marketed by the company UNION CARBIDE, having the chemical structure:

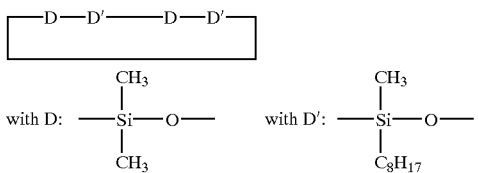

There may also be mentioned mixtures of cyclic silicones with organic compounds derived from silicon, such as the mixture of octamethylcyclotetrasiloxane and tetratrimethylsilylpentaerythritol (50/50) and the mixture of octamethylcyclotetrasiloxane and 1,1'-oxy(2,2,2',2',3,3'-hexatrimethylsilyloxy)bisneopentane;

(ii) linear volatile silicones having 2 to 9 silicon atoms and possessing a viscosity of less than or equal to $5 \times 10^{-6}$ m$^2$/s at 25° C. It is for example the decamethyltetrasiloxane marketed in particular under the name "SH 200" by the company TORAY SILICONE. Silicones entering into this class are also described in the article published in Cosmetics and Toiletries, Vol. 91, Jan. 76, p. 27–32—TODD & BYERS "Volatile Silicone fluids for cosmetics".

Nonvolatile silicones and more particularly polyalkylsiloxanes, polyarylsiloxanes, polyalkylarylsiloxanes, silicone gums and resins, polyorganosiloxanes modified by organofunctional groups and mixtures thereof are preferably used.

These silicones are more particularly chosen from polyalkylsiloxanes among which there may be mentioned mainly polydimethylsiloxanes with terminal trimethylsilyl groups having a viscosity of $5 \times 10^{-6}$ to 2.5 m$^2$/s at 25° C. and preferably $1 \times 10^{-5}$ to 1 m$^2$/s. The viscosity of the silicones is, for example, measured at 25° C. according to the ASTM 445 Appendix C standard.

Among these polyalkylsiloxanes, there may be mentioned, without limitation, the following commercial products:

SILBIONE® oils of the 47 and 70 047 series or MIRASIL® oils marketed by RHODIA such as, for example, the 70 047 V 500 000 oil;

oils of the MIRASIL® series marketed by the company RHODIA;

oils of the 200 series from the company DOW CORNING such as more particularly DC200 having a viscosity of 60 000 mm$^2$/s;

VISCASIL® oils from GENERAL ELECTRIC and certain oils of the SF series (SF 96, SF 18) from GENERAL ELECTRIC.

There may also be mentioned the polydimethylsiloxanes with terminal dimethylsilanol groups known under the name dimethiconol (CTFA), such as the oils of the 48 series from the company RHODIA.

In this class of polyalkylsiloxanes, there may also be mentioned the products marketed under the names "ABIL WAX® 9800 and 9801" by the company GOLDSCHMIDT which are poly($C_1$–$C_{20}$)alkylsiloxanes.

The polyalkylarylsiloxanes are particularly chosen from polydimethyl/methylphenylsiloxanes, polydimethyldiphenylsiloxanes which are linear and/or branched and have a viscosity of $1 \times 10^{-5}$ to $5 \times 10^{-2}$ m$^2$/s at 25° C.

Among these polyalkylarylsiloxanes, there may be mentioned, by way of example, the products marketed under the following names:

SILBIONE® oils of the 70 641 series from RHODIA;

oils of the RHODORSIL® 70 633 and 763 series from RHODIA;

DOW CORNING 556 COSMETIC GRAD FLUID oil from DOW CORNING;

silicones of the PK series from BAYER such as the product PK20;

silicones of the PN, PH series from BAYER such as the products PN1000 and PH1000;

certain oils of the SF series from GENERAL ELECTRIC such as SF 1023, SF 1154, SF 1250, SF 1265.

The silicone gums which can be used in accordance with the invention are in particular polydiorganosiloxanes having high number-average molecular masses of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisabutylenes, methylene chloride, pentane, dodecane, tridecane or mixtures thereof.

The following products may be more particularly mentioned:

polydimethylsiloxane polydimethylsiloxane/methylvinylsiloxane gums, polydimethylsiloxane/diphenylsiloxane, polydimethylsiloxane/phenylmethylsiloxane, polydimethylsiloxane/diphenylsiloxane/methylvinylsiloxane.

Products which can be more particularly used in accordance with the invention are mixtures such as:

the mixtures formed from a polydimethylsiloxane hydroxylated at the chain end or dimethiconol (CTFA) and from a cyclic dimethylsiloxane also called cyclomethicone (CTFA) such as the product Q2 1401 marketed by the company DOW CORNING;

the mixtures formed from a polydimethylsiloxane gum with a cyclic silicone such as the product SF 1214 Silicone Fluid from the company GENERAL ELECTRIC; this product is a gum SF 30 corresponding to a dimethicone, having a number-average molecular weight of 500 000, solubilized in the oil SF 1202 Silicone Fluid corresponding to decamethylcyclopentasiloxane;

the mixtures of two PDMSs of different viscosities, and more particularly of a PDMS gum and a PDMS oil, such as the product SF 1236 from the company GENERAL ELECTRIC. The product SF 1236 is the mixture of an SE 30 gum defined above having a viscosity of 20 m$^2$/s and an SF 96 oil having a viscosity of $5 \times 10^{-6}$ m$^2$/s. This product preferably comprises 15% of SE 30 gum and 85% of an SF 96 oil.

The organopolysiloxane resins which can be used in accordance with the invention are crosslinked siloxane systems containing the units:

$R_2SiO_{2/2}$, $R_3SiO_{1/2}$, $RSiO_{3/2}$ and $SiO_{4/2}$ in which R represents a hydrocarbon group possessing 1 to 16 carbon atoms or a phenyl group. Among these products, those particularly preferred are those in which R denotes a $C_1$–$C_4$ lower alkyl, more particularly methyl, group or a phenyl group.

There may be mentioned among these resins the product marketed under the name "DOW CORNING 593" or those marketed under the names "SILICONE FLUID SS 4230 and SS 4267" by the company GENERAL ELECTRIC and which are silicones having the dimethyl/trimethylsiloxane structure.

There may also be mentioned the resins of the trimethylsilyloxysilicate type which are marketed in particular under the names X22-4914, X21-5034 and X21-5037 by the company SHIN-ETSU.

The organomodified silicones which can be used in accordance with the invention are silicones as defined above and comprising in their structure one or more organofunctional groups attached via a hydrocarbon group.

Among the organomodified silicones, there may be mentioned the polyorganosiloxanes comprising:

polyethyleneoxy and/or polypropyleneoxy groups optionally comprising $C_6$–$C_{24}$ alkyl groups such as the oils called dimethicone-copolyol marketed by the company DOW CORNING under the name DC 1248 or the oils SILWET® L 722, L 7500, L 77, L 711 from the company UNION CARBIDE and the ($C_{12}$)alkyl-methicone-copolyol marketed by the company DOW CORNING under the name Q2 5200;

substituted or unsubstituted amine-containing groups such as the products marketed under the name GP 4 Silicone Fluid and GP 7100 by the company GENESEE or the products marketed under the names Q2 8220 and DOW CORNING 929 or 939 by the company DOW CORNING. The substituted amine-containing groups are in particular $C_1$–$C_4$ aminoalkyl groups;

thiol groups, such as the products marketed under the names "GP 72 A" and "GP 71" from GENESEE;

alkoxylated groups, such as the product marketed under the name "SILICONE COPOLYMER F-755" by SWS SILICONES and ABIL WAX® 2428, 2434 and 2440 by the company GOLDSCHMIDT;

hydroxylated groups, such as the polyorganosiloxanes with a hydroxyalkyl functional group which are described in French patent application FR-A-85 16334;

acyloxyalkyl groups such as, for example, the polyorganosiloxanes described in patent U.S. Pat. No. 4,957,732;

anionic groups of the carboxylic type, such as, for example, in the products described in EP Patent 186 507 from the company CHISSO CORPORATION, or of the alkylcarboxylic type such as those present in the product X-22-3701E from the company SHIN-ETSU; 2-hydroxyalkylsulphonate; 2-hydroxyalkylthiosulphate such as the products marketed by the company GOLDSCHMIDT under the names "ABIL® S201" and "ABIL® S255";

hydroxyacylamino groups, such as the polyorganosiloxanes described in application EP 342 834. There may be mentioned, for example, the product Q2-8413 from the company DOW CORNING.

The silicones as described above may be used alone or as a mixture, in a quantity of between 0.01 and 20% by weight, preferably between 0.1 and 5% by weight.

The composition according to the invention may comprise one or more vegetable oils such as sweet almond oil, avocado oil, castor oil, olive oil, jojoba oil, sunflower oil, wheat germ oil, sesame oil, groundnut oil, grape seed oil, soya-bean oil, rapeseed oil, safflower oil, copra oil, maize oil, hazelnut oil, shea butter, palm oil, apricot stone oil, calophyllum oil, and mixtures thereof.

As ceramides which can be used in the composition according to the invention, there may be mentioned in particular the ceramides of classes I, II, III and V according to the DOWNING classification (Downing, Donald T. et al, "Essential Fatty Acids and Epidermal Integrity," *Arch Dermatol*, Vol. 123, October 1987, pp. 1381–1383) and mixtures thereof, and more particular N-oleyldehydrosphingosine.

As anionic polymer which can be used in the present invention, there may be mentioned in particular polymers comprising groups derived from carboxylic, sulphonic or phosphoric acids, and having a weight-average molecular mass of between 500 and 5 000 000.

The carboxylic groups are provided by unsaturated mono- or dicarboxylic acid monomers such as those

corresponding to the formula:

in which n is an integer from 0 to 10, A denotes a methylene group, optionally linked to the carbon atom of the unsaturated group or to the neighbouring methylene group when n is greater than 1, via a heteroatom such as oxygen or sulphur, $R_1$ denotes a hydrogen atom, or a phenyl or benzyl group, $R_2$ denotes a hydrogen atom, a carboxyl or lower alkyl group, $R_3$ denotes a hydrogen atom or a lower alkyl group, a group —$CH_2$—COOH, or a phenyl or benzyl group.

In the above formula, a lower alkyl group preferably comprises from 1 to 4 carbon atoms and denotes in particular the methyl and ethyl groups.

The anionic polymers with carboxylic groups preferred according to the invention are:

A) the homo- or copolymers of acrylic or methacrylic acid or their salts and in particular the products sold under the names VERSICOL® E or K by the company ALLIED COLLOID and ULTRAHOLD® by the company BASF, the copolymers of acrylic acid and of acrylamide sold in the form of their sodium salt under the names RETEN® 421, 423 or 425 by the company HERCULES, the sodium salts of the polyhydroxycarboxylic acids;

B) The copolymers of acrylic or methacrylic acids with a monoethylene monomer such as ethylene, styrene, vinyl esters, acrylic or methacrylic acid esters, optionally grafted onto a polyalkylene glycol such as polyethylene glycol and optionally crosslinked. Such polymers are described in particular in French Patent 1,222,944 and German Application 2,330,956, copolymers of this type containing in their chain an acrylamide unit optionally N-alkylated and/or hydroxyalkylated as described especially in Luxembourg Patent applications 75370 and 75371 or offered under the name QUADRAMER® by the company AMERICAN CYANAMID. There may also be mentioned the copolymers of acrylic acid and $C_1$–$C_4$ alkyl methacrylate and the copolymer of methacrylic acid and ethyl acrylate sold under the name LUVIMER® MAEX by the company BASF.

C) The copolymers derived from crotonic acid such as those containing in their chain vinyl propionate or acetate units and optionally other monomers such as methallyl or allyl esters, vinyl ether or vinyl ester of a linear or branched saturated carboxylic acid with a long hydrocarbon chain such as those containing at least 5 carbon atoms, it being possible for these polymers to be optionally grafted and crosslinked or alternatively a vinyl, allyl or methallyl ester of an α- or β-cyclic carboxylic acid. Such polymers are described, inter alia, in French Patents 1,222,944; 1,580,545; 2,265,782; 2,265,781; 1,564,110 and 2,439,798. Commercial products entering into this class are the resins 28-29-30, 26-13-14 and 28-13-10 sold by the company NATIONAL STARCH.

D) The polymers derived from maleic, fumaric or itaconic acids or anhydrides and vinyl esters, vinyl ethers, vinyl halides, phenylvinyl derivatives, acrylic acid and its esters; these polymers may be esterified. Such polymers are described in particular in U.S. Pat. Nos. 2,047,398, 2,723, 248 and 2,102,113, and GB Patent GB 839 805, and in particular those sold under the names GANTREZ® AN or ES by the company ISP.

The polymers also entering into this class are the copolymers of maleic, citraconic or itaconic anhydrides and an allyl or methallyl ester optionally comprising an acrylamide or methacrylamide group, an α-olefin, acrylic or methacrylic esters, acrylic or methacrylic acids or vinylpyrrolidone in their chain; the anhydride functional groups are monoesterified or monoamidated. These polymers are for example described in French patents 2 350 384 and 2 357 241 by the applicant.

E) The polyacrylamides containing carboxylate groups.

The polymers comprising sulphonic groups are polymers containing vinylsulphonic, styrenesulphonic, naphthalenesulphonic or acrylamidoalkylsulphonic units.

These polymers may be especially chosen from:
the salts of polyvinylsulphonic acid having a molecular mass of between about 1000 and 100,000 as well as the copolymers with an unsaturated comonomer such as acrylic or methacrylic acids and their esters as well as acrylamide or its derivatives, vinyl ethers and vinylpyrrolidone;
the salts of polystyrenesulphonic acid, the sodium salts having a molecular mass of about 500,000 and about 100,000 sold respectively under the names Flexan® 500 and Flexan® 130 by National Starch. These compounds are described in FR Patent 2,198,719;
the salts of polyacrylamidesulphonic acids, such as those mentioned in U.S. Pat. No. 4,128,631 and more particularly polyacrylamidoethylpropanesulphonic acid sold under the name COSMEDIA POLYMER® HSP 1180 by Henkel.

According to the invention, the anionic polymers are preferably chosen from the acrylic acid copolymers such as the terpolymer acrylic acid/ethyl acrylate/N-tertbutylacrylamide sold under the name ULTRAHOLD® STRONG by the company BASF, the copolymers derived from crotonic acid such as the terpolymers vinyl acetate/vinyl tert-butylbenzoate/crotonic acid and the terpolymers crotonic acid/vinyl acetate/vinyl neododecanoate sold under the name Résine 28-29-30 by the company NATIONAL STARCH, the polymers derived from itaconic, fumaric and maleic acids or anhydrides with vinyl esters, vinyl ethers, vinyl halides, phenylvinyl derivatives, acrylic acid and its esters such as the monoesterified maleic anhydride/methylvinyl ether copolymer sold under the name GANTREZ® ES 425 by the company ISP, the copolymers of methacrylic acid and of methyl methacrylate sold under the name EUDRAGIT® L by the company ROHM PHARMA, the copolymer of methacrylic acid and of ethyl acrylate sold under the name LUVIMER® MAEX by the company BASF, the copolymer vinyl acetate/crotonic acid sold under the name LUVISET® CA 66 by the company BASF and the terpolymer vinyl acetate/crotonic acid/polyethylene glycol under the name ARISTOFLEX® A by the company BASF.

The anionic polymers most particularly preferred are those chosen from the monoesterified maleic anhydride/methylvinyl ether copolymer sold under the name GANTREZ® ES 425 by the company ISP, the copolymers of methacrylic acid and of methyl methacrylate sold under the name EUDRAGIT® L by the company ROHM PHARMA, the copolymer of methacrylic acid and ethyl acrylate sold under the name LUVIMER® MAEX by the company BASF, the terpolymer vinylpyrrolidone/acrylic acid/lauryl methacrylate sold under the name ACRYLIDONE® LM by the company ISP.

According to the invention, the anionic polymers may also be used in the form of a latex or pseudolatex, that is to say in the form of an aqueous dispersion of insoluble polymer particles.

The amphotene polymers which can be used in accordance with the invention may be chosen from the polymers containing B and C units distributed statistically in the polymer chain where B denotes a unit which is derived from a monomer containing at least one basic nitrogen atom and C denotes a unit which is derived from an acidic monomer containing one or more carboxylic or sulphonic groups or alternatively B and C may denote groups which are derived from zwitterionic monomers of carboxybetaines or of sulphobetaines;

B and C may also denote a cationic polymer chain containing primary, secondary, tertiary or quaternary amine groups, in which at least one of the amine groups carries a carboxylic or sulphonic group linked via a hydrocarbon group or alternatively B and C form part of a chain of a polymer with an α,β-dicarboxylic ethylene unit in which one of the carboxylic groups has been caused to react with a polyamine containing one or more primary or secondary amine groups.

The amphoteric polymers corresponding to the definition given above which are more particularly preferred are chosen from the following polymers:
(1) the polymers resulting from the copolymerization of a monomer derived from a vinyl compound carrying a carboxylic group such as more particularly acrylic acid, methacrylic acid, maleic acid, alpha-chloroacrylic acid, and of a basic monomer derived from a substituted vinyl compound containing at least one basic atom such as more particularly dialkylaminoalkyl methacrylate and acrylate, dialkylaminoalkylmethacrylamide and acrylamide. Such compounds are described in U.S. Pat. No. 3,836,537. There may also be mentioned the sodium acrylate/acrylamidopropyltrimethylammonium chloride copolymer sold under the name POLYQUART® KE 3033 by the company HENKEL.

The vinyl compound may also be a dialkyldiallylammonium salt such as diethyldiallylammonium chloride.

The copolymers of acrylic acid and of the latter monomer are provided under the names MERQUAT® 280, MERQUAT® 295 and MERQUAT® PLUS 3330 by the company CALGON.

(2) The polymers containing units which are derived from:
  a) at least one monomer chosen from acrylamides or methacrylamides substituted on the nitrogen by an alkyl group,
  b) at least one acidic comonomer containing one or more reactive carboxylic groups, and
  c) at least one basic comonomer such as esters with primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides more particularly preferred according to the invention are compounds whose alkyl groups contain from 2 to 12 carbon atoms and more particularly N-ethylacrylamide, N-tertbutylacrylamide, N-tert-octylacrylamide, N-octylacrylamide, N-decylacrylamide, N-dodecylacrylamide as well as the corresponding methacrylamides.

The acidic comonomers are chosen more particularly from acrylic, methacrylic, crotonic, itaconic, maleic and fumaric acids as well as the alkyl monoesters having 1 to 4 carbon atoms of maleic or fumaric anhydrides or acids.

The basic comonomers preferred are methacrylates of aminoethyl, butylaminoethyl, N,N'-dimethylaminoethyl, N-tert-butylaminoethyl.

Particularly used are the copolymers whose CTFA name (4th ed. 1991) is Octylacrylamide/acrylates/butylaminoethylmethacrylate copolymer such as the products sold under the name AMPHOMER® or LOVOCRYL® 47 by the company NATIONAL STARCH.

(3) The partially or completely acylated and crosslinked polyaminoamides derived from polyaminoamides of general

formula:

in which $R'_0$ represents a divalent group derived from a saturated dicarboxylic acid, a mono- or dicarboxylic aliphatic acid with ethylenic double bond, an ester of a lower alkanol having 1 to 6 carbon atoms of these acids or a group which is derived from the addition of any one of the said acids with a bis-primary or bis-secondary amine, and Z denotes a group which is derived from a bis-primary, mono- or bis-secondary polyalkylene-polyamine and preferably represents:

a) in the proportions of 60 to 100 mol %, the

group where x=2 and p=2 or 3, or alternatively x=3 and p=2 this group being derived from the diethylenetriamine, triethylenetetraamine or dipropylenetriamine;

b) in the proportions of 0 to 40 mol %, the group (XI) above, in which x=2 and p=1 and which is derived from ethylenediamine, or the group which is derived from piperazine:

c) in the proportions of 0 to 20 mol %, the group —NH—(CH$_2$)$_6$—NH— which is derived from hexamethylenediamine, these polyamino amines being crosslinked by adding a bifunctional crosslinking agent chosen from the epihalohydrins, diepoxides, dianhydrides, bis-unsaturated derivatives, by means of 0.025 to 0.35 mol of crosslinking agent per amine group of the polyamino amide and acylated by the action of acrylic acid, chloroacetic acid or of an alkanesultone or of their salts.

The saturated carboxylic acids are preferably chosen from the acids having 6 to 10 carbon atoms such as adipic, 2,2,4-trimethyladipic and 2,4,4-trimethyladipic acid, terephthalic acid, the acids with ethylene double bond such as for example acrylic, methacrylic and itaconic acids. The alkanesultones used in the acylation are preferably propane- or butanesultone, the salts of the acylating agents are preferably the sodium or potassium salts.

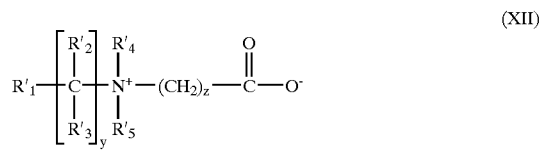

(4) The polymers containing zwitterionic units of formula: in which $R'_1$ denotes a polymerizable unsaturated group such as an acrylate, methacrylate, acrylamide or methacrylamide group, y and z each represent an integer from 1 to 3, $R'_2$ and $R'_3$ represent a hydrogen atom, a methyl, ethyl or propyl group, $R'_4$ and $R'_5$ represent a hydrogen atom or an alkyl group such that the sum of the carbon atoms in $R'_4$ and $R'_5$ does not exceed 10.

The polymers comprising such units may also comprise units derived from nonzwitterionic monomers such as dimethyl- or diethylaminoethyl acrylate or methacrylate or alkyl acrylates or methacrylates, acrylamides or methacrylamides or vinyl acetate.

By way of example, there may be mentioned the copolymer of methyl methacrylate/methyl dimethylcarboxymethylammonioethyl methacrylate such as the product sold under the name DIAFORMER® Z301 by the company SANDOZ.

(5) The polymers derived from chitosan containing monomeric units corresponding to the following formulae:

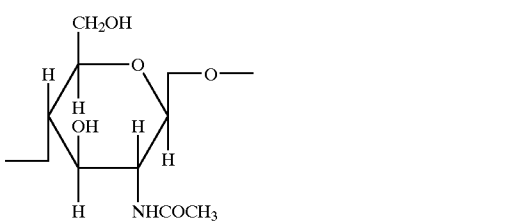

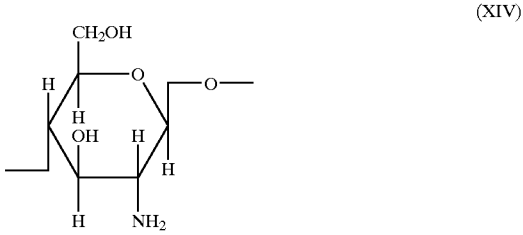

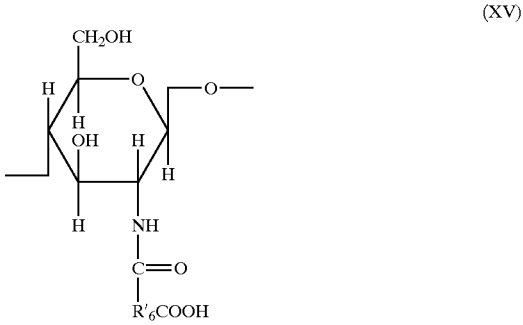

the (XIII) unit being present in proportions of between 0 and 30%, the (XIV) unit in proportions of between 5 and 50% and the (XV) unit in proportions of between 30 and 90%, it being understood that in this (XV) unit, $R'_6$ represents a group of formula:

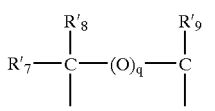

in which if q=0, $R'_7$, $R'_8$ and $R'_9$, which are identical or different, each represent a hydrogen atom, a methyl, hydroxyl, acetoxy or amino residue, a monoalkylamine residue or a dialkylamine residue optionally interrupted by one or more nitrogen atoms and/or optionally substituted with one or more amine, hydroxyl, carboxyl, alkylthio or sulphonic groups, or an alkylthio residue whose alkyl group carries an amino residue, at least one of the $R'_7$, $R'_8$ and $R'_9$ groups being in this case a hydrogen atom; or if q=1, $R'_7$, $R'_8$ and $R'_9$ each represent a hydrogen atom, as well as the salts formed by these compounds with bases or acids.

(6) The polymers derived from the N-carboxyalkylation of chitosan such as N-carboxymethyl chitosan or N-carboxybutyl chitosan sold under the name EVALSAN® by the company JAN DEKKER.

(7) The polymers corresponding to the general formula

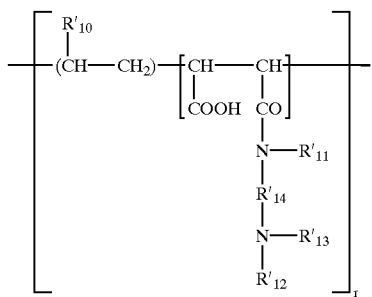

(XVII) described for example in French Patent 1,400,366: in which $R'_{10}$ represents a hydrogen atom, a $CH_3O$, $CH_3CH_2O$ or phenyl group, $R'_{11}$ denotes hydrogen or a lower alkyl group such as methyl or ethyl, $R'_{12}$ denotes hydrogen or a lower alkyl group such as methyl or ethyl, $R'_{13}$ denotes a lower alkyl group such as methyl or ethyl or a group corresponding to the formula: $—R'_{14}—N(R'_{12})_2$, $R'_{14}$ representing a group $—CH_2—CH_2—$, $—CH_2—CH_2—CH_2—$ or $—CH_2—CH(CH_3)—$, $R'_{12}$ having the meanings mentioned above, as well as the higher homologues of these groups and containing up to 6 carbon atoms.

(8) Amphoteric polymers of the —D—X—D—X— type chosen from:

a) the polymers obtained by the action of chloroacetic acid or sodium chloroacetate on the compounds containing at least one unit of formula:

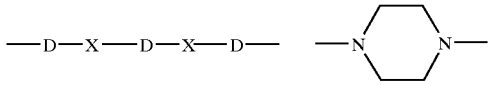

where D denotes a group
and X denotes the symbol E or E', E or E', which are identical or different, denote a bivalent group which is an alkylene group with a linear or branched chain containing up to 7 carbon atoms in the principal chain which is unsubstituted or substituted with hydroxyl groups and which may contain, in addition, oxygen, nitrogen or sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, or hydroxyl, benzylamine, amine oxide, quaternary ammonium, amide, imide, alcohol, ester and/or urethane groups.

b) The polymers of formula:

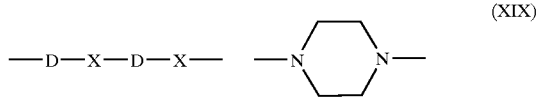

where D denotes a group
and X denotes the symbol E or E' and, at least once, E'; E having the meaning indicated above and E' is a bivalent group which is an alkylene group with a linear or branched chain having up to 7 carbon atoms in the principal chain, which is unsubstituted or substituted with one or more hydroxyl groups and containing one or more nitrogen atoms, the nitrogen atom being substituted with an alkyl chain optionally interrupted by an oxygen atom and necessarily containing one or more carboxyl functional groups or one or more hydroxyl functional groups and betainized by reaction with chloroacetic acid or sodium chloroacetate.

(9) The copolymers $(C_1–C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl comonomers such as vinylcaprolactam.

The amphoteric polymers which are particularly preferred according to the invention are those of the family (1) or (2).

The cosmetically acceptable aqueous medium may consist solely of water or of a mixture of water and a cosmetically acceptable solvent such as a $C_1–C_4$ lower alcohol, such as ethanol, isopropanol, tert-butanol, n-butanol; alkylene glycols such as propylene glycol, polyol ethers; $C_5–C_{10}$ alkanes; acetone, methyl ethyl ketone; $C_1–C_4$ alkyl acetates such as methyl acetate, ethyl acetate, butyl acetate; dimethoxyethane, diethoxyethane; and mixtures thereof.

The pH of the compositions of the invention is between 4 and 8, preferably between 5 and 7.

The compositions according to the invention may also contain additives such as associative or non-associative, anionic, amphoteric, zwitterionic, nonionic or cationic, natural or synthetic polymeric thickeners, nonpolymeric thickeners such as acids or electrolytes, pearlescent agents, opacifying agents, organic solvents, perfumes, mineral, vegetable and/or synthetic oils, fatty acid esters, colorants, organic particles, preservatives, pH-stabilizing agents.

Persons skilled in the art will be careful to choose the optional additives and their quantity so that they do not damage the properties of the compositions of the present invention.

These additives are present in the composition according to the invention in a quantity ranging from 0 to 20% by weight relative to the total weight of the composition.

The compositions may be provided in the form of fluid or thickened liquids, gels, creams, foams, water-in-oil (W/O), oil-in-water (O/W) emulsions or multiple emulsions.

They may be used, for example, as shampoos, rinse-out treatments, deep treatment masks, lotions or creams for treating the scalp.

The present invention also relates to a method for the cosmetic treatment of the keratinous fibres which consists in applying an effective quantity of a composition as described above, to the keratinous fibres, in rinsing after an optional exposure time.

According to a preferred embodiment of the invention, the composition may be used as a shampoo.

The following example illustrates the present invention and should not be considered in any manner as limiting the invention.

EXAMPLE

A shampoo is prepared from the ingredients indicated in the table below. The quantities are indicated as % by weight relative to the total weight of the composition.

| | |
|---|---|
| Aluminium oxide[1] | 0.5 |
| Sodium lauryl ether sulphate (2.2 mol of ethylene oxide) at 26% of active substance | 47.5 |
| JR400 (AMERCHOL) | 0.5 |
| Water | qs 100 |
| pH | 6.5 |

[1]having a mean primary particle size in numerical terms of 13 nm, sold under the name ALUMINIUMOXID C by the company DEGUSSA-HULS.

The shampoo according to the invention is applied to the hair, rinsed and the hair is dried.

The keratinous fibres are strengthened and the hair can be styled better.

What is claimed is:

1. A composition for washing keratinous materials, comprising, in a cosmetically acceptable aqueous medium, particles consisting essentially of aluminium oxide and having a mean primary size of less than 200 nm, at least one conditioning agent soluble or insoluble in the cosmetically acceptable aqueous medium, the conditioning agent being a cationic surfactant, a cationic polymer, a silicone, a vegetable oil, a ceramide, an anionic polymer, an amphoteric polymer or mixtures thereof, and at least one detergent surfactant, said composition not simultaneously containing an anionic surfactant and an amphoteric or nonionic surfactant.

2. The composition according to claim 1, wherein the mean primary size of the particles is between 5 and 50 nm.

3. The composition according to claim 1, wherein the aluminium oxide is alumina or hydrated alumina.

4. The composition according to claim 3, wherein the aluminium oxide is boehmite.

5. The composition according to claim 1, wherein the particles are present in a concentration of 0.01 to 20% by weight relative to the total weight of the composition.

6. The composition according to claim 5, wherein the particles are present in a concentration of 0.1 to 5% by weight relative to the total weight of the composition.

7. The composition according to claim 1, wherein the detergent surfactant is an anionic, amphoteric or nonionic surfactant.

8. The composition according to claim 1, wherein the surfactant is present in a quantity of between 1 and 50% by weight relative to the total weight of the composition.

9. The composition according to claim 8, wherein the surfactant is present in a quantity of between 5 and 35% by weight relative to the total weight of the composition.

10. The composition according to claim 1, wherein the cationic surfactant is a salt of an optionally polyoxyalkylenated primary, secondary or tertiary fatty amine; a quaternary ammonium salt which is a tetraalkylammonium, alkylamidoalkyltrialkylammonium, trialkylbenzylammonium, trialkylhydroxyalkylammonium or alkylpyridinium chloride or bromide, an imidazoline derivative; or an amine oxide with a cationic character; or mixtures thereof.

11. The composition according to claim 1, wherein the cationic polymer is a derivative of cellulose ether comprising a quaternary ammonium group, a cationic cyclopolymer, a modified guar gum, a quaternary polymer of vinylpyrrolidone and vinylimidazole, a polycondensate of polyquaternary ammonium, or mixtures thereof.

12. The composition according to claim 1, wherein the cationic polymer is present in a quantity of between 0.0001 and 10% by weight.

13. The composition according to claim 1, wherein the weight ratio between the cationic polymer and the aluminium oxide is between 100 and 0.0005.

14. The composition according to claim 1, wherein the silicone is volatile or nonvolatile, cyclic or acyclic, branched or unbranched, organomodified or nonorganomodified.

15. The composition according to claim 14, wherein the silicone is a cyclic volatile silicone comprising from 3 to 7 silicon atoms, a linear volatile silicone having 2 to 9 silicon atoms and possessing a viscosity of less than or equal to $5 \times 10^{-6}$ m$^2$/s at 25° C.; a nonvolatile silicone which is a polyalkylsiloxane, polyarylsiloxane, polyalkylarylsiloxane, a silicone gum or resin, a polyorganosiloxane modified by an organofunctional group which is a polyethyleneoxy or propyleneoxy group or mixtures thereof, a substituted or unsubstituted amine-containing group, a thiol, an alkoxylated or hydroxylated group, an acyloxyalkyl, carboxylic acid or hydroxyacylamino group, or mixtures thereof.

16. The composition according to claim 1, wherein the vegetable oil is a sweet almond oil, an avocado oil, a castor oil, an olive oil, a jojoba oil, a sunflower oil, a wheat germ oil, a sesame oil, a groundnut oil, a grape seed oil, a soya-bean oil, a rapeseed oil, a safflower oil, a copra oil, a maize oil, a hazelnut oil, a shea butter, a palm oil, an apricot stone oil, a calophyllum oil, or mixtures thereof.

17. The composition according to claim 1, wherein the ceramide is a ceramide of classes I, II, II or V according to the DOWNING classification, or mixtures thereof.

18. The composition according to claim 1, wherein the anionic polymer is a polymer comprising a group derived from a carboxylic, sulphonic or phosphoric acid, and having a weight-average molecular mass of between 500 and 5,000,000.

19. The composition according to claim 1, wherein the amphoteric polymer is:
  (1) a polymer resulting from the copolymerization of a monomer derived from a vinyl compound carrying a carboxylic group, and of a basic monomer derived from a substituted vinyl compound containing at least one basic atom, or
  (2) a polymer containing units which are derived from:
    a) at least one monomer which is an acrylamide or methacrylamide substituted on the nitrogen by a $C_{2-12}$ alkyl group,
    b) at least one acidic comonomer containing one or more reactive carboxylic groups, and
    c) at least one basic comonomer which is an ester with a primary, secondary, tertiary or quaternary amine substituent of acrylic or methacrylic acid or the product of quaternization of dimethylaminoethyl methacrylate with dimethyl or diethyl sulphate.

20. The composition according to claim 1, wherein the cosmetically acceptable aqueous medium consists solely of water or of a mixture of water and a cosmetically acceptable solvent.

21. The composition according to claim 20, wherein the cosmetically acceptable solvent is a $C_1$–$C_4$ lower alcohol, an alkylene glycol, a $C_5$–$C_{10}$, acetone, methyl ethyl ketone, a $C_1$–$C_4$ alkyl acetate, dimethoxyethane, diethoxyethane or mixtures thereof.

22. The composition according to claim 1, wherein the composition further comprises an associative or non-associative, anionic, amphoteric, zwitterionic, nonionic or cationic, natural or synthetic polymeric thickener, a non-polymeric thickener, a pearlescent agent, an opacifying agent, an organic solvent, a perfume, a colorant, an organic particle, a preservative or a pH-stabilizing agent.

23. The composition of claim 1, wherein the composition is a shampoo.

24. A method for the cosmetic treatment of keratinous fibres, comprising applying a washing composition to the keratinous fibres and rinsing the keratinous fibres, the washing composition comprising, in a cosmetically acceptable aqueous medium, particles consisting essentially of aluminium oxide and having a mean primary size of less than 200 nm, at least one conditioning agent soluble or insoluble in the cosmetically acceptable aqueous medium, the conditioning agent being a cationic surfactant, a cationic polymer, a silicone, a vegetable oil, a ceramide, an anionic polymer, an amphoteric polymer or mixtures thereof, and at least one detergent surfactant, said composition not simultaneously containing an anionic surfactant and an amphoteric or nonionic surfactant.

* * * * *